United States Patent
Sanjay-Gopal et al.

(10) Patent No.: US 6,187,018 B1
(45) Date of Patent: Feb. 13, 2001

(54) AUTO POSITIONER

(75) Inventors: Sethumadavan Sanjay-Gopal, Mayfield Heights; Dale A. Messner, Uniontown; Bernard J. Czarkowski, Stow, all of OH (US)

(73) Assignee: Z-Kat, Inc., Hollywood, FL (US)

( * ) Notice: Under 35 U.S.C. 154(b), the term of this patent shall be extended for 0 days.

(21) Appl. No.: 09/429,127

(22) Filed: Oct. 27, 1999

(51) Int. Cl.$^7$ .................................................. A61B 19/00
(52) U.S. Cl. ...................... 606/130; 606/129; 604/116; 600/426; 600/427
(58) Field of Search .................................. 606/130, 129, 606/1; 604/116; 600/407, 410, 414, 426, 417, 429; 128/665, 653.1; 378/206, 205, 163, 164, 166

(56) References Cited

U.S. PATENT DOCUMENTS

| | | | |
|---|---|---|---|
| 5,776,064 | * 7/1998 | Kalfas et al. | 600/414 |
| 5,891,034 | * 4/1999 | Bucholz | 600/427 |
| 5,902,239 | * 5/1999 | Buurman | 600/427 |
| 5,967,982 | * 10/1999 | Barnett | 606/130 |
| 6,006,126 | * 12/1999 | Cosman | 606/426 |
| 6,006,127 | * 12/1999 | Van Der Brug et al. | 606/130 |
| 6,013,087 | * 1/2000 | Adams et al. | 606/130 |

OTHER PUBLICATIONS

Picker International, Inc., "ViewPoint 4.0 User's Guide," pp. i–x, 1, 2 and 24–27, 1998.

* cited by examiner

*Primary Examiner*—Pedro Philogene
(74) *Attorney, Agent, or Firm*—Fay, Sharpe, Fagan, Minnich & McKee, LLP

(57) ABSTRACT

A detector unit (20) for an image guided surgery system (10) is provided. It includes an adjustable stand (22) having a plurality of receivers (24) mounted thereto such that the detector unit (20) has a predefined finite field of view (80) in which it detects radiant energy. It further includes at least one light source (90) mounted to the adjustable stand (22) in fixed relation to the receivers (24). The at least one light source (90) projects visible light in a predetermined pattern to mark a location of the field of view (80).

21 Claims, 3 Drawing Sheets

AUTO POSITIONER

BACKGROUND OF THE INVENTION

The present invention relates to the medical diagnostic imaging and surgical arts. It finds particular application in conjunction with image guided surgery (IGS), and will be described with particular reference thereto. However, it is to be appreciated that the present invention is also amenable to other like applications.

Medical diagnostic imaging is a valuable tool for obtaining accurate visualization of a particular patient's internal anatomy and/or pathology in a minimally invasive manner. Prior to a medical procedure, three-dimensional (3D) diagnostic image data of the brain, spinal cord, and/or other anatomy of interest is often generated by computed tomography (CT) scanners, magnetic resonance imaging (MRI) scanners, gamma cameras, and other medical diagnostic imaging equipment. Typically, these imaging modalities provide structural detail with a resolution of a millimeter or better. Reconstructed images of the patients anatomy are then used by medical personnel to aid in navigating through and/or around various anatomical structures during surgery.

Commonly, an IGS system includes a computer, active and/or passive tools carrying infra-red (IR) emitting diodes, a stereoscopic optical tracking system, and a tool interface device. The IR rays emitted by the active tool (or reflected in the case of a passive tool) are detected by charge-coupled device (CCD) cameras mounted on an optical unit. Using the detected IR rays, the system tracks and/or localizes the position and orientation of the tool in a 3D coordinate space which is registered with that of the 3D image data. In this manner, the position and trajectory of a tool relative to imaged anatomy is determined and used to aid in the maneuvering of the tool and/or the placement of a tool guide.

Various frameless stereotactic IGS procedures have been developed which take advantage of the 3D image data of the patient. These procedures include guided-needle biopsies, shunt placements, craniotomies for lesion or tumor resection, total hip replacement (THR) surgery, and the like. Another area of frameless stereotaxy procedures which requires extreme accuracy is spinal surgery, including screw fixation, fracture decompression, and spinal tumor removal.

In spinal screw fixation procedures, for example, surgeons or other medical personnel tap and drill a hole in spinal vertebra into which a screw is to be placed. The surgeon often relies heavily on his own skill in placing and orienting the bit of the surgical drill prior to forming the hole in the vertebra. Success depends largely upon the surgeon's estimation of anatomical location and orientation in the operative field. Unaided, this approach can lead to less than optimal placement of screws which in turn may injure nerves, blood vessels, or the spinal cord.

In THP surgery, the surgeon aligns an implant cup in a pre-planned orientation suing the assistance of the navigation system. The cup is optimally oriented so as to allow a maximum range of motion for the leg (i.e., femur) without impinging on the pelvic bone.

Nevertheless, use of a stereotactic IGS procedure presents certain problems and/or complications of its own. For example, one problem is obtaining the correct positioning of the CCD cameras such that their focus and/or finite field of view (FOV) are optimally located relative to a patient's anatomy of interest. This can be extremely important for some procedures such as, for example, THR wherein the navigation system has to track the movements of two objects (i.e., the pelvis and the femur) with respect to each other. Trackers used to localize these two objects may be as far apart as 1–2 feet, and the navigation system has to be optimally positioned so that both trackers are within the FOV of the system.

Previously developed techniques aimed at achieving a solution to this problem involved complicated software design, and indirect feedback. In turn, only specially trained personnel were qualified to set up the system.

The present invention contemplates a new and improved auto-positioning device which overcomes the above-referenced problems and others.

SUMMARY OF THE INVENTION

In accordance with one aspect of the present invention, a detector unit for an image guided surgery system is provided. It includes an adjustable stand having a plurality of receivers mounted thereto such that the detector unit has a defined finite field of view in which it detects radiant energy. It further includes at least one source of radiant energy mounted to the adjustable stand in fixed relation to the receivers. The source projects radiant energy in a pattern to mark a location of the defined field of view.

In accordance with a more limited aspect of the present invention, the at least one source is a light source.

In accordance with a more limited aspect of the present invention, the light source is a laser.

In accordance with a more limited aspect of the present invention, the at least one source of radiant energy includes a plurality of sources.

In accordance with a more limited aspect of the present invention, the sources of radiant energy are arranged such that projected radiant energy therefrom is concentrated at a point in space which coincides with a location in the defined field of view.

In accordance with a more limited aspect of the present invention, the location in the defined field of view is selected from a group consisting of its center and one of its outer boundaries.

In accordance with a more limited aspect of the present invention, the pattern marks at least one dimension of the defined field of view.

In accordance with a more limited aspect of the present invention, the light source includes first and second light sources. The first light source projects a ring of light at a defined distance which marks the location of the defined field of view. The second light source projects a beam of light which intersects the ring of light at the defined distance. At the defined distance, the ring of light has a diameter substantially equal to that of the defined field of view.

In accordance with a more limited aspect of the present invention, the first and second light sources are lasers and the first light source has a refractive element affixed to an output end thereof. The refractive element forms light emitted from the first light source into a substantially conically shaped beam.

In accordance with another aspect of the present invention, a method of positioning a finite field of view of a detector unit for an image guided surgery system is provided. The method includes holding a light reflecting surface at a point in space and projecting a pattern of light from the detector unit toward the light reflecting surface. The pattern of light has a fixed spatial relationship with respect to the detector unit's field of view. Thereafter, the light reflecting surface is viewed, and the detector unit and light reflecting surface are adjusted relative to one another until a desired pattern of light is depicted on the light reflecting surface.

In accordance with a more limited aspect of the present invention, the method further includes determining spatial coordinates for the field of view based upon the light reflecting surface's position.

In accordance with a more limited aspect of the present invention, the step of projecting includes projecting at least two laser beams of light which intersect at a predetermined location relative to the field of view.

In accordance with a more limited aspect of the present invention, the detector unit is adjusted until the intersection coincides with where the light reflecting surface is being held such that a single dot is viewed thereon.

In accordance with a more limited aspect of the present invention, the desired pattern of light viewed on the light reflecting surface coincides with the field of view and has at least one dimension in common therewith.

In accordance with a more limited aspect of the present invention, the light reflecting surface has indicia thereon which correspond to the desired pattern of light which is being sought.

In accordance with another aspect of the present invention, a field of view targeting system for an image guided surgery system having a detector unit which tracks the orientation and position of surgical tools within a defined field of view is provided. The field of view targeting system includes a plurality of sources which project a pattern of radiant energy. The pattern of radiant energy is spatially fixed relative to the defined field of view.

In accordance with a more limited aspect of the present invention, the sources are light sources which project radiant energy as beams of light.

In accordance with a more limited aspect of the present invention, the field of view targeting system further includes a detection means for detecting the radiant energy.

In accordance with a more limited aspect of the present invention, the detection means includes a surface which intercepts the radiant energy such that the pattern is discernable at a location of the surface.

In accordance with a more limited aspect of the present invention, the pattern of radiant energy marks a dimension of the defined field of view.

In accordance with a more limited aspect of the present invention, the pattern of radiant energy traces a periphery of the defined field of view.

One advantage of the present invention is its simplicity and ease of use.

Another advantage of the present invention is that it provides first hand visual feedback to personnel positioning the system.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
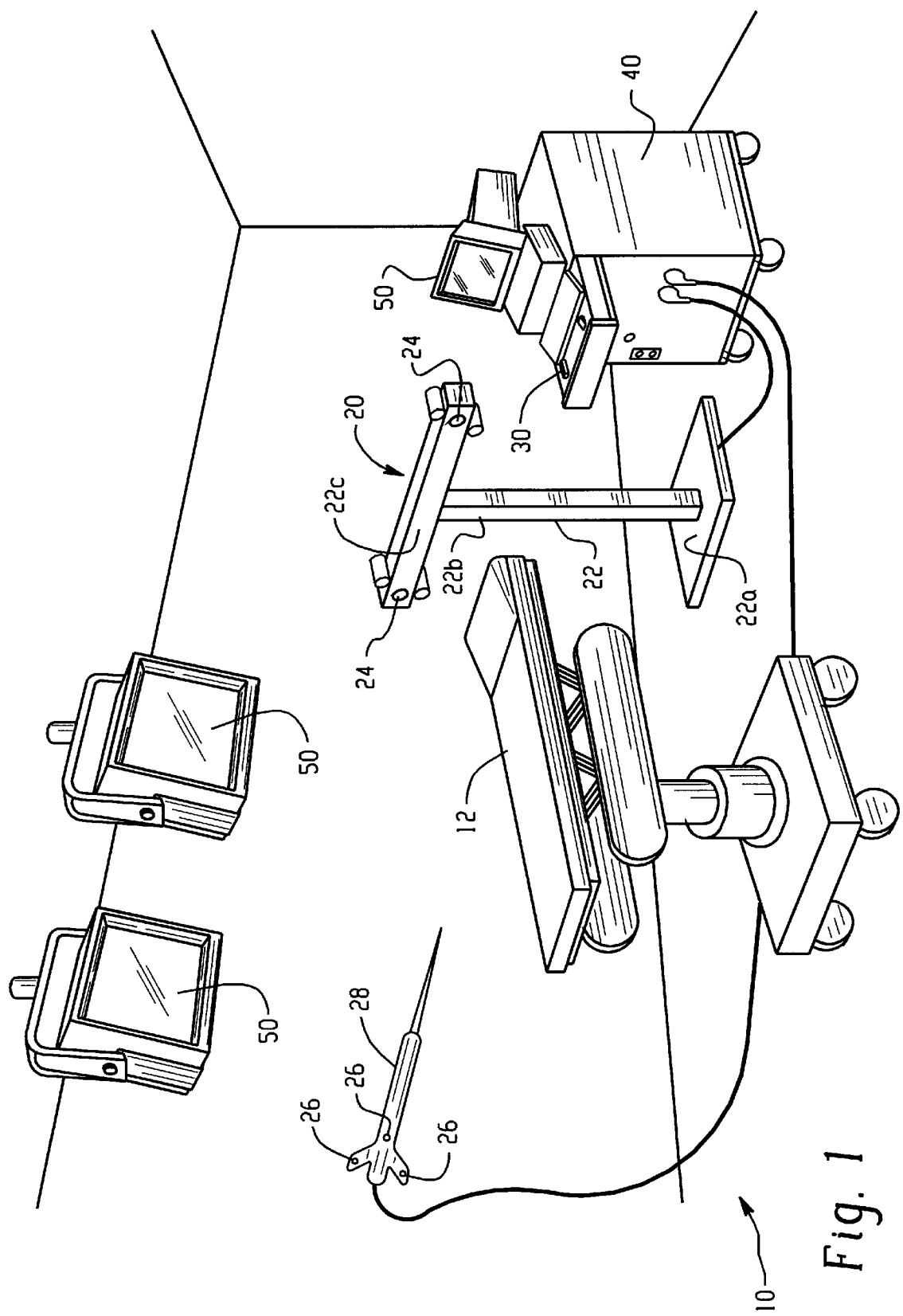
FIG. 1 is a diagrammatic illustration of an image guided surgery system in accordance with aspects of the present invention; and, FIGS. 2A–C are diagrammatic illustrations showing the operation of an auto-positioning system in accordance with aspects of the present invention.

With reference to FIG. 1, an IGS system is indicated generally by reference numeral 10. In use, a subject, such as a human patient, is received on an operating table, couch, or other subject support 12 and appropriately positioned within the operating room. Securing means, such as a head clamp (not shown) or patient restraint straps (not shown), securely position or fix at least a portion of the subject under consideration to the subject support 12.

A detector unit 20 is positioned in relationship to the patient such that its precise location and orientation within a coordinate system of the subject or subject support 12 is maintained throughout the medical procedure being performed. In the illustrated embodiment, the detector unit 20 includes an adjustable stand 22 having: a base 22a upon which the stand 22 is balanced; a vertically extending portion 22b rising from the base 22a; and, an elongated head 22c attached to the vertically extending portion 22b at an end opposite the base 22a. The stand 22 has multiple degrees of freedom of movement to adjust the height of the vertically extending portion 22b, and to adjust the tilt, cant, and/or rotation of the elongated head 22c. Optionally, the base 22a has selectively lockable wheels or coasters (not shown) mounted thereunder to facilitate the stand's movement as desired. Additionally, the stand 22 includes locking mechanisms (not shown) that are used to fix the orientation of the stand 22 and prevent further movement about its degrees of freedom. Optionally, the stand 22 is mounted to the patient support 12. This permits the patient support 12 to be turned, raised, lowered, wheeled to another location, or the like, without altering the patient's coordinate system relative to the stand 22. Alternately, the stand 22 is mounted to a pole or other stationary support, the ceiling of the room, or the like.

The stand 22 supports a plurality of receivers 24, such as CCD arrays, IR cameras, light sensitive diodes, other light sensitive receivers, or the like, mounted at fixed, known locations thereon. In a preferred embodiment, as illustrated, two receivers 24 are mounted at opposite ends of the elongated head 22c. Alternately, the receivers 24 receive other types of radiant energy, such as ultrasound, x-ray radiation, radio waves, magnetic waves, or the like.

The receivers 24 detect radiation of the selected type received from passive or active emitters 26 transmitting the same. In this manner, the detection unit 20 resolves or tracks the spatial location of the emitters. The emitters 26 are affixed to different objects to track their location in real space. For example, they are optionally affixed to a surgical tool, such as the illustrated probe or wand 28, a biopsy needle, a needle guide, etc. Accordingly, the relative orientations and positions of objects with attached emitter, e.g., wand 28, are determined.

Preferably, control and/or coordination of the IGS system 10 is carried out via an operator console 30 housing a computer system 40. Alternately, the computer system 40 can be remotely located and connected with the operator console 30 by appropriate cabling or otherwise. The computer system 40 stores or otherwise accesses three-dimensional (3D) image data from which image representations of the subject are selected or generated for display on video monitors 50 or other appropriate image rendering devices. Optionally, the image representations are two-dimensional (2D) planes or slices selected from, e.g., axial, sagittal, coronal, or oblique planes through a selected point on the subject.

Registration of the subject in real space with images of the same in image space is carried out in a usual manner, e.g., by identification of three or more corresponding points in each space which are used to define a transformation matrix between real space and image space. Optionally, the corresponding points are readily recognizable anatomical markers. Alternately fiducials which are visualized or otherwise recognizable in the image are affixed to the subject prior to imaging. In any event, by tracking a surgical tool (e.g., the wand 28) in real space (which is registered with image space) with the detection unit 20, a graphic representation of the surgical tool is mapped to image space where it is visualized along with the image representation of the subject via the video monitors 50. In this manner then, interventionalists or other medical personnel viewing the video monitors 50 are aided in navigating through and/or around various anatomical structures.

Figure 2A:
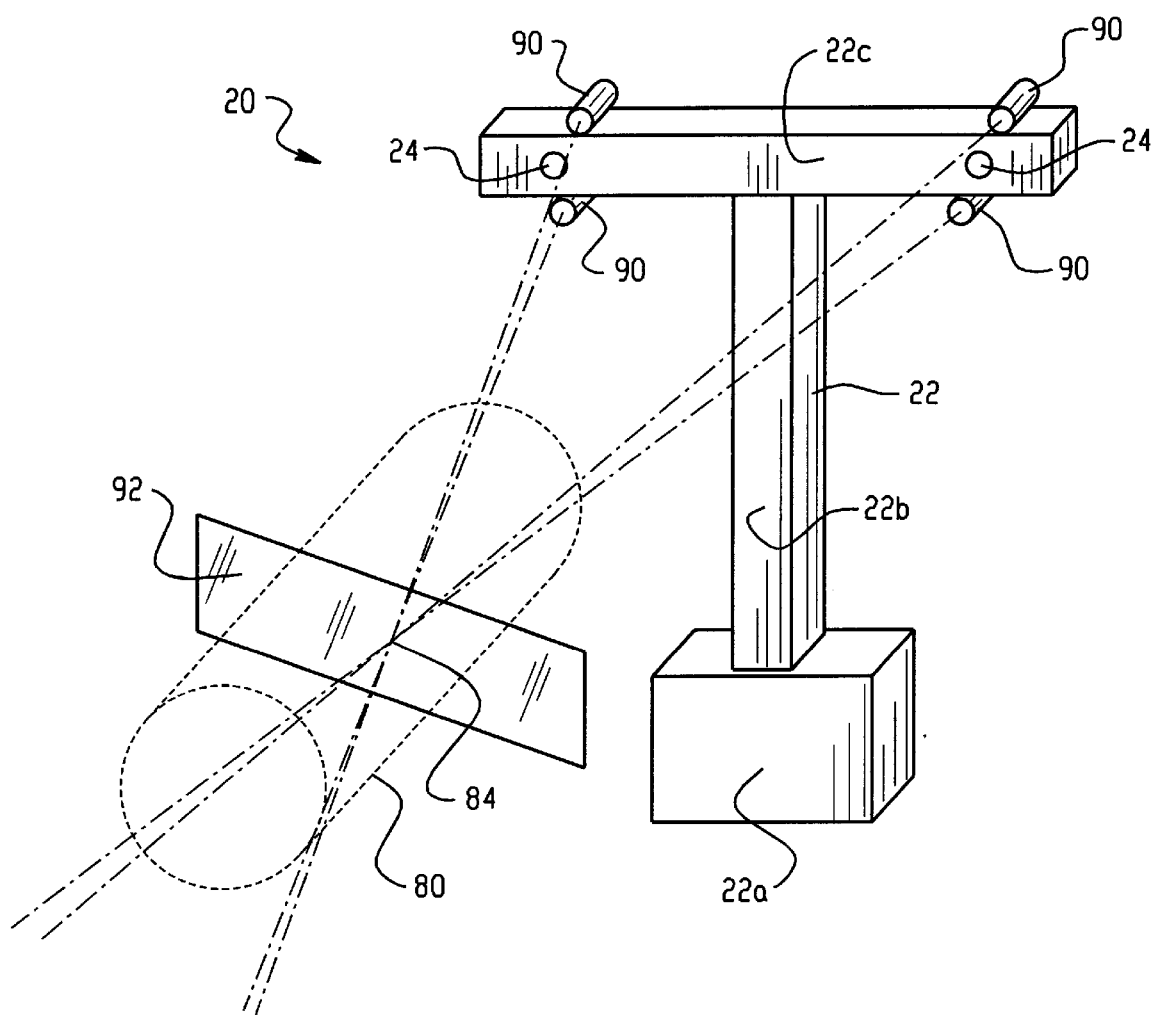
Figure 2B:
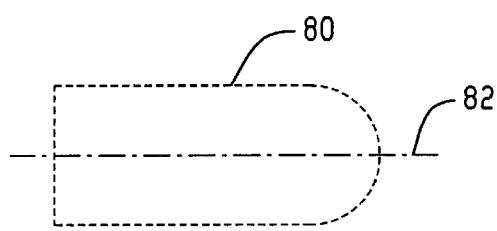

With reference to FIGS. 2A and 2B and continuing reference to FIG. 1, the detector unit 20 has a finite FOV 80 which is defined by the particular configuration of receivers 24 employed. In a preferred embodiment such as the one illustrated with two receivers 24 mounted at opposite ends of the head 22c, the FOV 80 is bullet shaped (i.e., cylindrical with a hemispherical cap at the end proximate the detector unit 20). FIG. 2B shows a longitudinal cross-section of the FOV 80 taken at its central axis 82. In operation, the detector unit 20 is adjusted (via adjustments to the stand 22) and/or positioned to target the FOV 80 in a desired region such that the emitters 26 remain in the FOV 80 during use of the wand 28 for the medical procedure being performed. Emitters located outside the FOV 80 are not accurately detected and/or resolved by the IGS system 10. Hence, when the emitters on the wand 28 do not fall within the FOV 80, the wand's trajectory and coordinate location is not accurately determined.

In a preferred embodiment, targeting of the FOV 80 is achieved with a set of visible light sources 90 and an ancillary reflecting surface 92. The visible light sources 90 are preferably low power lasers, for example, the type used in laser pointers, and the ancillary reflecting surface 92 is preferably a rigid white card. The visible light sources 90 are mounted on the stand 22 of the detector unit 20 in fixed relation to the receivers 24. The light sources 90 are arranged such that when the ancillary reflecting surface 92 is held at a distance in front thereof, the pattern or patterns of visible light on the surface 92 indicate the location of the FOV 80.

More specifically, with reference to FIG. 2A, in a preferred embodiment, there are four low-power laser light sources 90 arranged on the elongated head 22c in fixed relation to the receivers 24 such that their beams intersect at the center 84 of the FOV 80 regardless of the adjustment to or positioning of the stand 22. The lasers are low-power in the sense that they are sufficiently weak so as not to harm an individual coming into contact with their beams. To locate and/or position the center 84 of the FOV 80, either or both the ancillary reflecting surface 92 and the detector unit 20 are moved and/or adjusted until the pattern of visible light produced on the surface 92 is a single dot indicating the point of intersection of the four beams of light from each source 90 and consequently indicating the center 84 of the FOV 80. Optionally, more or as few as two light sources 90 are employed. Additionally, the point of intersection of the light beams optionally marks points within the FOV 80 other than the center 84, for example, in alternate embodiments it marks either end of the FOV 80. Another alternative includes using multiple light sources 90 having multiple intersection points to mark a plurality of points within and/or at the surface of the FOV 80. In the case of marking the FOV 80 with a plurality of intersection points, multiple ancillary reflecting surfaces 92 are optionally used to locate/position the points and consequently locate/position the FOV 80.

Figure 2C:
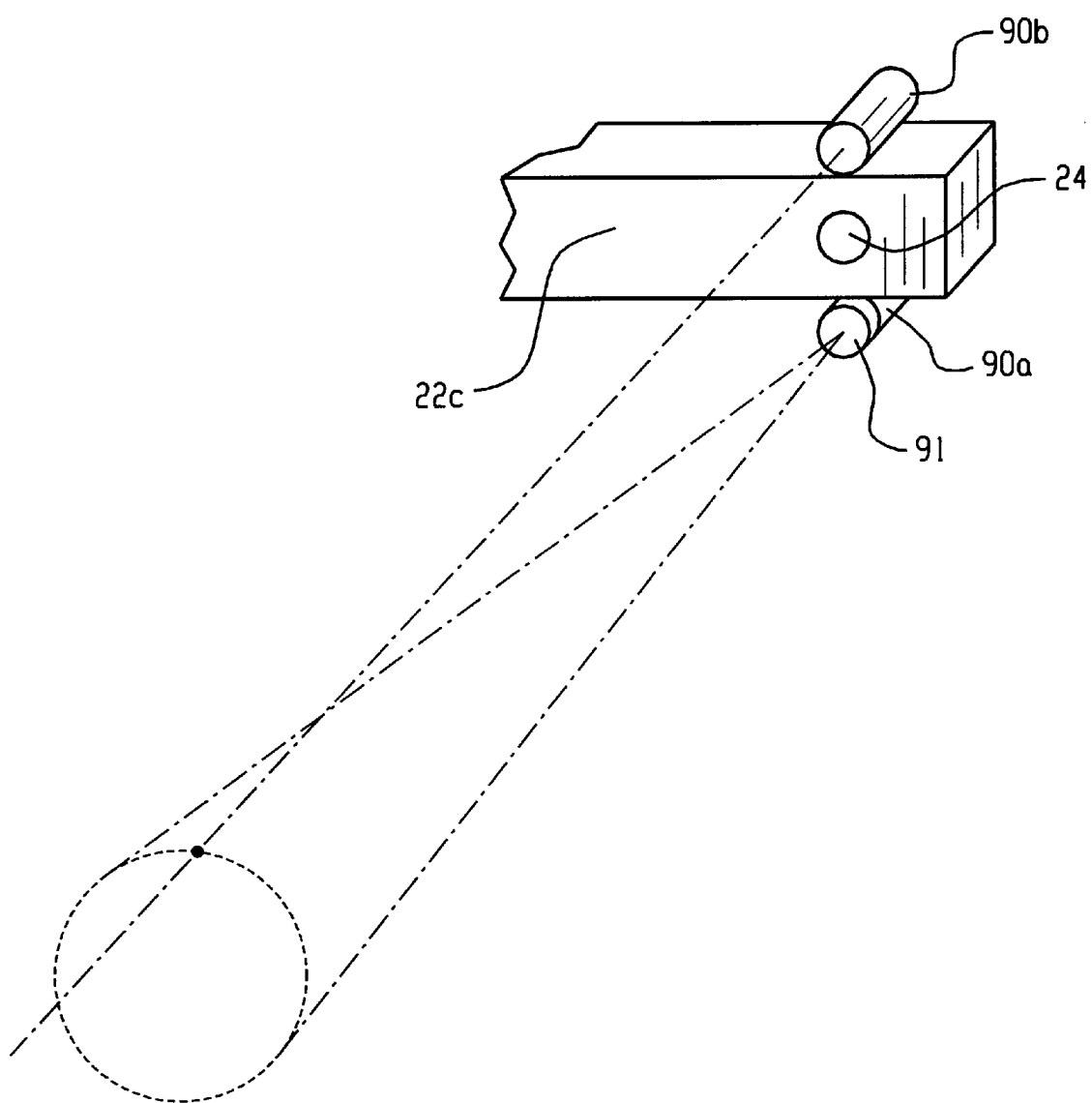

With reference to FIG. 2C, in an alternate embodiment, at least one low power laser light source 90a is fitted with a diffuser or refractive element 91 that spreads its light beam into a cone such that at progressively greater distances it forms a ring of progressively greater diameter on the ancillary reflecting surface 92. A second source 90b is angularly disposed with respect to the source 90a such that its beam intersects the surface of the cone at a distance from the detector unit 20 where the FOV 80 and the ring formed on the surface 92 have the same diameter. Optionally, the intersection marks the center of the FOV's cylindrical portion, either end, or any other desired point, depending on the spread angle of the element 91 and the offset angle of the second source 90b. In alternate preferred embodiments, the shape of the light beam emanating from the laser light source 90a is achieved by affixing the laser light source 90a to a rotating disk or other gyrating member. Alternately, an angularly disposed rotating mirror or other deflector shapes the beam of light from the laser light source 90a. Moreover, the shape or trajectory of the light beam is optionally altered to trace the outline or periphery along one or more dimensions of different fields of view having selected shapes as determined by the configuration and/or number of receivers 24 being employed.

For further assurance of accurate FOV targeting, the ancillary reflective surface 92 optionally includes registration marks thereon such that when the surface 92 is located at a predefined position within the FOV 80, the pattern of light from the sources 90 coincides with the registration marks. For example, in a preferred embodiment, the registration mark is a ring, and a source 90 with element 91 projects a diverging cone of light. When the surface 92 is located at a predetermined position in the FOV 80 the projection coincides with the registration mark. In this manner, if the projection appears to be out of round for example, the surface 92 is tilted or canted with respect to a central axis 82 of the FOV 80. Optionally, the registration mark is elongated to account for a cone of light from a source 90 not on the central axis 82 of the FOV 80. In the alternative, the cone of light is elongated.

In alternate preferred embodiments, detectable forms of radiant energy other than visible light are employed in targeting the FOV 80. That is to say, optionally, the sources 90 emit electro-magnetic radiation, ultrasound or other like acoustic radiation, IR or other like non-visible radiation, radio waves, etc. In these embodiments, rather than the simple reflective surface 92, a receiver (including, e.g., a configuration of detectors for sensing the selected form or forms of radiation) is employed to detect the pattern of radiation emanating from sources 90 fixed in relation to the FOV 80. Upon detecting the pattern of radiation indicating the location of the FOV 80, the receiver triggers a human perceivable signal (e.g., visual or audible) indicating to an operator that the pattern has been detected, and hence the FOV 80 located. For example, sources of detectable radiant energy are optionally arranged such that a convergence or concentration of radiant energy is focused at a fixed point relative to the FOV 80. In this manner then, when a determined level or intensity of radiant energy is detect by the receiver, which level is sufficiently high to indicate the convergence or concentration of radiant energy, that point of focus is located and the FOV 80 is readily determined relative thereto. Alternately, multiple points of focus or different patterns of radiant energy, fixed in relation to the FOV 80, are used to locate the FOV 80 in real space.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A detector unit for an image guided surgery system comprising:

an adjustable stand;

a plurality of receivers mounted to the adjustable stand such that the detector unit has a finite defined field of view in which it detects radiant energy; and, at least one source of radiant energy mounted to the adjustable stand in fixed relation to the receivers,, said source projecting radiant energy in a pattern to mark a location of the defined field of view.

2. The detector unit according to claim 1, wherein said at least one source is a light source.

3. The detector unit according to claim 2, wherein the light source is a laser.

4. The detector unit according to claim 1, wherein the at least one source of radiant energy includes a plurality of sources.

5. The detector unit according to claim 4, wherein the sources of radiant energy are arranged such that projected radiant energy therefrom is concentrated at a point in space which coincides with a location in the defined field of view.

6. The detector unit according to claim 5, wherein the location in the defined field of view is selected from a group consisting of its center and one of its outer boundaries.

7. The detector unit according to claim 1, wherein the pattern marks at least one dimension of the defined field of view.

8. The detector unit according to claim 2, wherein the light source includes:

a first light source, said first light source projecting a ring of light at a defined distance which marks the location of the defined field of view; and, a second light source, said second light source projecting a beam of light which intersects the ring of light at the defined distance;

wherein at the defined distance the ring of light has a diameter substantially equal to that of the defined field of view.

9. The detector unit according to claim 8, wherein the first and second light sources are lasers and the first light source has a refractive element affixed to an output end thereof, said refractive element forming light emitted from the first light source into a substantially conically shaped beam.

10. A method of positioning a finite field of view of a detector unit for an image guided surgery system, the method comprising:

(a) holding a surface at a point in space;

(b) projecting a pattern of light from the detector unit toward the surface, said pattern of light having a fixed spatial relationship with respect to the detector unit's field of view;

(c) viewing the surface; and, (d) adjusting the detector unit and surface relative to one another until a desired pattern of light is viewed on the surface.

11. The method according to claim 10, further comprising:

(e) determining spatial coordinates for the field of view based on the surface's position.

12. The method according to claim 10, wherein the step of projecting includes:

projecting at least two laser beams of light which intersect at a predetermined location relative to the field of view.

13. The method according to claim 12, wherein the detector unit is adjusted until the intersection coincides with where the surface is being held such that a single dot is viewed thereon.

14. The method according to claim 10, wherein the desired pattern of light viewed on the surface coincides with the field of view and has at least one dimension in common therewith.

15. The method according to claim 14, wherein the surface has indicia thereon which correspond to the desired pattern of light which is being sought.

16. A field of view targeting system for an image guided surgery system having a detector unit which tracks the orientation and position of surgical tools within a defined field of view, said field of view targeting system comprising:

a plurality of sources which project a pattern of radiant energy, said pattern of radiant energy being spatially fixed relative to the defined field of view.

17. The field of view targeting system according to claim 16, wherein the sources are light sources which project radiant energy as beams of light.

18. The field of view targeting system according to claim 16, wherein the field of view targeting system further includes a detection means for detecting the radiant energy.

19. The field of view targeting system according to claim 18, wherein the detection means includes a surface which intercepts the radiant energy such that the pattern is discernable at a location of the surface.

20. The field of view targeting system according to claim 16, wherein said pattern of radiant energy marks a dimension of the defined field of view.

21. The field of view targeting system according to claim 16, wherein said pattern of radiant energy traces a periphery of the defined field of view.

\* \* \* \* \*